United States Patent
Schultz et al.

(10) Patent No.: US 10,392,660 B2
(45) Date of Patent: *Aug. 27, 2019

(54) ALTERNATIVE NUCLEOTIDE FLOWS IN SEQUENCING-BY-SYNTHESIS METHODS

(71) Applicant: LIFE TECHNOLOGIES CORPORATION, Carlsbad, CA (US)

(72) Inventors: Jonathan Schultz, Oxford, MA (US); John Davidson, Guilford, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 15/404,735

(22) Filed: Jan. 12, 2017

(65) Prior Publication Data

US 2017/0121766 A1    May 4, 2017

Related U.S. Application Data

(60) Division of application No. 13/689,252, filed on Nov. 29, 2012, now Pat. No. 9,605,308, which is a continuation of application No. 13/157,865, filed on Jun. 10, 2011, now abandoned.

(60) Provisional application No. 61/354,173, filed on Jun. 11, 2010.

(51) Int. Cl.
    *B01L 3/00*     (2006.01)
    *C12Q 1/6869*   (2018.01)
    *C12Q 1/6874*   (2018.01)

(52) U.S. Cl.
    CPC ......... *C12Q 1/6869* (2013.01); *C12Q 1/6874* (2013.01); *B01L 3/5027* (2013.01)

(58) Field of Classification Search
    None
    See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,210,015 A | 5/1993 | Gelfand et al. | |
| 5,399,491 A | 3/1995 | Kacian et al. | |
| 5,750,341 A | 5/1998 | Macevicz | |
| 5,854,033 A | 12/1998 | Lizardi | |
| 6,174,670 B1 | 1/2001 | Wittwer et al. | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,404,907 B1 | 6/2002 | Gilchrist et al. | |
| 6,780,591 B2 | 8/2004 | Williams et al. | |
| 6,828,100 B1 | 12/2004 | Ronaghi | |
| 6,833,246 B2 | 12/2004 | Balasubramanian | |
| 6,911,327 B2 | 6/2005 | McMillan et al. | |
| 7,037,687 B2 | 5/2006 | Williams et al. | |
| 7,049,645 B2 | 5/2006 | Sawada et al. | |
| 7,133,782 B2 | 11/2006 | Odedra | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,335,762 B2 | 2/2008 | Rothberg et al. | |
| 7,348,181 B2 | 3/2008 | Walt et al. | |
| 7,424,371 B2 | 9/2008 | Kamentsky | |
| 7,535,232 B2 | 5/2009 | Barbaro et al. | |
| 7,575,865 B2 | 8/2009 | Leamon et al. | |
| 7,645,596 B2 | 1/2010 | Williams et al. | |
| 7,782,237 B2 | 8/2010 | Ronaghi et al. | |
| 7,785,862 B2 | 8/2010 | Kim et al. | |
| 7,835,871 B2 | 11/2010 | Kain et al. | |
| 7,875,440 B2 | 1/2011 | Williams et al. | |
| 7,948,015 B2 | 5/2011 | Rothberg et al. | |
| 8,666,678 B2 | 3/2014 | Melville | |
| 9,416,413 B2 * | 8/2016 | Schultz | C12Q 1/6874 |
| 2003/0219797 A1 | 11/2003 | Zhao et al. | |
| 2004/0018506 A1 | 1/2004 | Koehler et al. | |
| 2004/0106138 A1 * | 6/2004 | Raskind | C12Q 1/6883 435/6.11 |
| 2004/0142330 A1 | 7/2004 | Nyren et al. | |
| 2004/0197793 A1 | 10/2004 | Hassibi et al. | |

(Continued)

FOREIGN PATENT DOCUMENTS

| | | |
|---|---|---|
| GB | 2461127 | 12/2009 |
| WO | WO-1999/057321 | 11/1999 |

(Continued)

OTHER PUBLICATIONS

Ronaghi et al. (2002) Discovery of single nucleotide polymorphisms and mutations by Pyrosequencing. Comparative and Functional Genomics, 3:51-56.*

Garcia et al. (2000) Mutation detection by pyrosequencing: sequencing of exons 5-8 of the p53 tumor suppressor gene. Gene, 253: 249-257.*

Non Final Office Action for U.S. Appl. No. 13/440,849, dated Aug. 15, 2015.

U.S. Appl. No. 13/859,360, Final Office Action dated Jul. 28, 2015, 15 pages.

U.S. Appl. No. 13/440,849, Final Office Action dated Dec. 16, 2014, 7 pp.

U.S. Appl. No. 13/859,673, Final Office Action dated Jun. 4, 2015, 22pp.

(Continued)

*Primary Examiner* — Neil P Hammell
(74) *Attorney, Agent, or Firm* — Jones Robb, P.L.L.C.

(57) ABSTRACT

A method of sequencing a polynucleotide strand can include providing the polynucleotide strand with a primer annealed thereto and a polymerase operably bound to the polynucleotide strand; successively exposing the polynucleotide strand to the flow of four different dNTPs according to a first predetermined ordering; and successively exposing the polynucleotide strand to the flow of four different dNTPs according to a second predetermined ordering, wherein the second predetermined ordering is different from the first predetermined ordering.

9 Claims, 9 Drawing Sheets

Specification includes a Sequence Listing.

(56) References Cited

U.S. PATENT DOCUMENTS

| | | |
|---|---|---|
| 2004/0197845 A1 | 10/2004 | Hassibi et al. |
| 2005/0084851 A1 | 4/2005 | Ronaghi et al. |
| 2006/0040297 A1 | 2/2006 | Leamon et al. |
| 2006/0147935 A1 | 7/2006 | Linnarsson |
| 2006/0147983 A1 | 7/2006 | O'uchi et al. |
| 2007/0059733 A1 | 3/2007 | Sundararajan et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0161195 A1 | 7/2008 | Turner et al. |
| 2008/0166727 A1 | 7/2008 | Esfandyarpour et al. |
| 2008/0182757 A1 | 7/2008 | Heiner et al. |
| 2008/0268454 A1 | 10/2008 | Denise et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1* | 5/2009 | Rothberg ............ C12Q 1/6874 257/253 |
| 2009/0137404 A1 | 5/2009 | Drmanac et al. |
| 2009/0176200 A1 | 7/2009 | Wakita et al. |
| 2009/0312188 A1 | 12/2009 | Duer et al. |
| 2010/0035252 A1 | 2/2010 | Rothberg et al. |
| 2010/0035253 A1 | 2/2010 | Gordon et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281264 A1 | 11/2011 | Abitol et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0264621 A1 | 10/2012 | Hubbell et al. |
| 2013/0172201 A1 | 7/2013 | Schultz et al. |
| 2013/0280702 A1 | 10/2013 | Schultz et al. |
| 2013/0288904 A1 | 10/2013 | Hubbell et al. |
| 2014/0031238 A1 | 1/2014 | Schultz et al. |
| 2017/0044602 A1 | 2/2017 | Hubbell et al. |

FOREIGN PATENT DOCUMENTS

| | | |
|---|---|---|
| WO | WO-2001/001015 | 1/2001 |
| WO | WO-2002/020837 | 3/2002 |
| WO | 2002062825 A2 | 8/2002 |
| WO | WO-2003/020895 | 3/2003 |
| WO | 2004001015 | 12/2003 |
| WO | 2004035741 A2 | 4/2004 |
| WO | WO-2005/040425 | 5/2005 |
| WO | WO-2007/098049 | 8/2007 |
| WO | WO-2008/076406 | 6/2008 |
| WO | WO-2008/092150 | 7/2008 |
| WO | WO-2008/092155 | 7/2008 |
| WO | WO-2009/158006 | 12/2009 |
| WO | WO-2010/047804 | 4/2010 |
| WO | 2010075188 | 7/2010 |
| WO | WO-2010/077859 | 7/2010 |
| WO | WO-2010/117804 | 10/2010 |
| WO | WO-2010/138182 | 12/2010 |
| WO | 2011064319 | 6/2011 |
| WO | WO-2011/120964 | 10/2011 |
| WO | WO-2011/156707 | 12/2011 |
| WO | WO-2012/058459 | 5/2012 |
| WO | 2012138921 | 10/2012 |

OTHER PUBLICATIONS

U.S. Appl. No. 13/859,673, Advisory Action dated Sep. 24, 2015, 4 pp.

15178097.0-1403, European Search Report dated Sep. 17, 2015, 5 pp.

U.S. Appl. No. 13/859,673, Non-Final Office Action dated Nov. 4, 2014, 21 pages.

CN 201280027883A, Office Action dated Sep. 22, 2014 and English translation, 12 pages.

U.S. Appl. No. 13/859,667, Non-Final Office Action dated Mar. 5, 2015, 38 pages.

U.S. Appl. No. 13/859,360, Non-Final Office Action dated Jan. 16, 2015, 11 pages.

U.S. Appl. No. 13/859,667, Final Office Action dated Oct. 10, 2014, 25 pages.

Rosenfeld, "Enumerating De Bruijin Sequences", Comm. Math. Comput. Chem. (MATCH), 43:41-48 (2001).

Rosenfeld, "Enumerating Kautz Sequences", Kragujevac J. Math., 24:19-41 (2002).

Garcia et al., "Mutation detection by pyrosequencing: sequencing of exons 5-8 of the p53 tumor suppressor gene", Gene, 253:249-257 (2000) (see whole document, including Fig. 4).

Extended European search report in EP Appl. No. 11793237 (PCT/US11/39973), dated Jan. 9, 2014 (7 pages).

Office Action in U.S. Appl. No. 13/859,667, dated Mar. 26, 2014 (18 pages).

Final Office Action in U.S. Appl. No. 13/859,673, dated Mar. 21, 2014 (16 pages).

Ahmadian et al., Single-Nucleotide Polymorphism Analysis by Pyrosequencing, Analytical Chemistry, 280:103-110 (2000).

Office Action in U.S. Appl. No. 13/859,673, dated Sep. 11, 2013 (18 pages).

Office Action in U.S. Appl. No. 13/859,360, dated Dec. 24, 2013 (10 pages).

Svantesson et al., "A mathematical model of the Pyrosequencing reaction system", Biophysical Chemistry, 100:129-145 (2004).

Specification & Drawings of U.S. Appl. No. 61/198,222, filed Nov. 4, 2008.

Appendix to the Specification of U.S. Appl. No. 61/198,222, filed Nov. 4, 2008.

International Preliminary Report on Patentability, International Appl. No. PCT/US2012/032418, dated Oct. 8, 2013.

** Non-Final Office Action in U.S. Appl. No. 13/859,252, dated Jan. 2, 2015.

** Final Office Action in U.S. Appl. No. 13/859,252, dated Jun. 30, 2015.

** Advisory Action in U.S. Appl. No. 13/859,252, dated Oct. 19, 2015.

** Non-Final Office Action in U.S. Appl. No. 13/859,252, dated Jun. 2, 2016.

** Notice of Allowance in U.S. Appl. No. 13/859,252, dated Sep. 13, 2016.

(56) References Cited

OTHER PUBLICATIONS

International Search Report and Written Opinion in PCT/US12/32418, dated Jul. 25, 2012.
International Search Report and Written Opinion in PCT/US11/39973, dated Feb. 3, 2012.
International Search Report Application No. 18151358.1 dated May 30, 2018.
Examiner's first report in Australian Appl. No. 2011226792 based on PCT/US11/39973, dated Nov. 25, 2011.
Non-final Office Action in U.S. Appl. No. 13/157,865, dated Jul. 30, 2012.
Non-final Office Action in U.S. Appl. No. 15/236,172, dated Jul. 27, 2018.
Ahmadian et al., "Pyrosequencing: History, biochemistry and future," *Clin. Chim. Acta*, 363:83-94 (2006).
Aksyonov et al., "Multiplexed DNA sequencing-by-synthesis," *Anal. Biochem.*, 348:127-138.
Anderson et al., "A System for Multiplexed Direct Electrical Detection of DNA Synthesis," *Sens. Actuat. B-Chem.*, 129(1):79-86 (2008).
Balzer et al., "Characteristics of 454 pyrosequencing data—enabling realistic simulation with flowsim," *Bioinformatics*, 26:i420-i425 (2010).
Berger et al., "Compact, universal DNA microarrays to comprehensively determine transcription-factor binding site specificities," *Nat. Biotechnol.*, 24(11):1429-1435 (2006).
Berstel et al., "The origins of combinatorics on words," *Eur. J. Combin.*, 28(3):996-1022.
Brockman et al., "Quality scores and SNP detection in sequencing-by-synthesis systems," *Genome Res.*, 18:763-770 (2008).
Chapter 2, "Machine-Learning Foundations: The Probabilistic Framework," in Baldi, P. & Brunak, S., "Bioinformatics: The Machine Learning Approach," $2^{nd}$ Ed., The MIT Press, 47-65 (2001).
De Bruijn, N.G., "Ackowledgement of priority to C. Flye Sainte-Marie on the counting of circular arrangements of $2^n$ zeros and ones that show each n-letter word exactly once," *T.H.-Report 75-WSK-06*, Technological University Eindhoven (1975).
Droege et al., "The Genome Sequencer FLXTM System—longer reads, more applications, straight forward bioinformatics and more complete data sets," *J. Biotechnol.*, 136:3-10 (2008).
Elahi et al., "Pyrosequencing: A Tool for DNA Sequencing Analysis," in Zhao, S. & Stodolsky, M., Eds., *Methods in Molecular Biology*, vol. 255, Humana Press Inc., pp. 211-219.
Fakhrai-Rad et al., "Pyrosequencing™: An Accurate Detection Platform for Single Nucleotide Polymorphisms," *Hum. Mutat.*, 19:479-485 (2002).
Eltoukhy et al., "Modeling and Base-Calling for DNA Sequencing-By-Synthesis," *2006 IEEE International Conference on Acoustics, Speech, and Signal Processing*, II:1032-1035 (2006).
Finotello et al., "Comparative analysis of algorithms for whole-genome assembly of pyrosequencing data," *Briefings in Bioinformatics Advance Access*, 1-12 (Oct. 21, 2011).
Fuller et al., "The challenges of sequencing by synthesis", *Nat. Biotechnol.* 27(11):1013-23 (2009).
Guarizadeh, B., "Method Development and Applications of Pyrosequencing Technology," Doctoral Dissertation, Royal Institute of Technology, Stockholm, Sweden (2003).
Hert et al., "Advantages and limitations of next-generation sequencing technologies: a comparison of electrophoresis and non-electrophoresis methods," *Electrophoresis*, 29(23):4618-26 (2008).
Huse et al., "Accuracy and quality of massively parallel DNA pyrosequencing," *Genome Biol.*, 8(7):R143.1-R143.9 (2007).
Ji et al., "BM-BC: A Bayesian method of base calling for Solexa sequence data," *Department of Biostatistics, The University of Texas M. D. Anderson Cancer Center, Houston, Texas, U.S.A.* (http://odin.mdacc.tmc.edu/~ylji/BMBC/bmbc-ie2.pdf), 1-27, 2010.
Langaee et al., "Genetic variation analyses by Pyrosequencing," *Mutat. Res.*, 573:96-102 (2005).
Leamon et al., "Cramming More Sequencing Reactions onto Microreactor Chips," *Chem. Rev.*, 107:3367-3376 (2007).
Ledergerber et al., "Base-calling for next-generation sequencing platforms," *Briefings in Bioinformatics Advance Access*, 12(5):489-497 (Jan. 18, 2011).
Margulies et al., Supplementary Methods for the article "Genome sequencing in microfabricated high-density picolitre reactors," *Nature*, 437:376-380 (2005), pp. 1-34.
Margulies et al., "Genome sequencing in microfabricated high-density picolitre reactors," *Nature*, 437:376-380 (2005).
Massingham et al., "All Your Base: a fast and accurate probabilistic approach to base calling," *European Bioinformatics Institute, Wellcome Trust Genome Campus*, Hinxton, Cambridgeshire, UK (http://www.ebi.ac.uk/goldman-srv/AYB/references/ayb_revised.pdf), Oct. 26, 2011, 1-26.
Metzker, "Emerging technologies in DNA sequencing," *Genome Res.*, 15:1767-1776 (2005).
Metzker, "Sequencing Technologies-the Next Generation," *Nat. Rev. Genet.*, 11:31-46, 2010.
Pourmand et al., "Direct electrical detection of DNA synthesis," *P. Natl. Adac. Sci. USA*, 103(17):6466-6470 (2006).
Pourmand et al., "Multiplex Pyrosequencing," *Nucleic Acids Res.*, 30(7)(e31):1-5 (2002).
Ronaghi, M, "Pyrosequencing Sheds Light on DNA Sequencing", *Genome Res.*, 11:3-11 (2001).
Ronaghi et al., "A Sequencing Method Based on Real-Time Pyrophosphate," *Science*, 281(5375):363-365 (1998).
Ronaghi et al., "Discovery of single nucleotide polymorphisms and mutations by Pyrosequencing," *Comp. Funct. Genom.*, 3:51-56 (2002).
Rosenfeld, "Enumerating De Bruijin Sequences", *Comm. Math. Comput. Chem.* (MATCH), 45:71-83 (2002).
Van Aardenne-Ehrenfest et al., "Circuits and Trees in Oriented Linear Graphs" *Simon Stevin*, 28:203-217 (1951).
U.S. Appl. No. 13/859,667, filed Apr. 9, 2013.
U.S. Appl. No. 13/859,360, filed Apr. 9, 2013.

\* cited by examiner

FIG. 3A

Cycle n – conventional flow ordering (ATGC)

| A | T | A | G | C | A | C | T | A | C | G | G | A | A | C | G | T | G | A | A | G | G | T |

| B | T | A | G | C | A | C | T | A | C | G | G | A | A | C | G | T | G | A | A | G | G | T |

Cycle n+1 – conventional flow ordering (ATGC)

| A | T | A | G | C | A | C | T | A | C | G | G | A | A | C | G | T | G | A | A | G | G | T |

| B | T | A | G | C | A | C | T | A | C | G | G | A | A | C | G | T | G | A | A | G | G | T |

Cycle n+2 – conventional flow ordering (ATGC)

| A | T | A | G | C | A | C | T | A | C | G | G | A | A | C | G | T | G | A | A | G | G | T |

| B | T | A | G | C | A | C | T | A | C | G | G | A | A | C | G | T | G | A | A | G | G | T |

Cycle n+3 – conventional flow ordering (ATGC)

| A | T | A | G | C | A | C | T | A | C | G | G | A | A | C | G | T | G | A | A | G | G | T |

| B | T | A | G | C | A | C | T | A | C | G | G | A | A | C | G | T | G | A | A | G | G | T |

FIG. 3B

Cycle n – conventional flow ordering (ATGC)

A | • | • | • |   |   |   |   |   |   |   |   |   |   |   |   |   |   |   |   |   |
--|---|---|---|---|---|---|---|---|---|---|---|---|---|---|---|---|---|---|---|---
  | T | A | G | C | A | C | T | A | C | G | G | A | A | C | G | T | G | A | A | G | G | T

B | • | x |   |   |   |   |   |   |   |   |   |   |   |   |   |   |   |   |   |   |
  | T | A | G | C | A | C | T | A | C | G | G | A | A | C | G | T | G | A | A | G | G | T

Cycle n+1 – alternate flow ordering (AGA-TCT-GAG-CTC)

Cycle n+2 – alternate flow ordering (AGA-TCT-GAG-CTC)

Cycle n+3 – alternate flow ordering (AGA-TCT-GAG-CTC)

FIG. 4A

Cycle n – conventional flow ordering (ATGC)

| X | • | • | • |   |   |   |   |   |   |   |   |   |   |   |
|---|---|---|---|---|---|---|---|---|---|---|---|---|---|---|
|   | T | A | G | C | A | A | C | G | T | G | A | A | G | T |

| Y | • | • | • | • |   |   |   |   |   |   |   |   |   |   |
|---|---|---|---|---|---|---|---|---|---|---|---|---|---|---|
|   | T | A | G | C | A | A | C | G | T | G | A | A | G | T |

40 — 42

Cycle n+1 – conventional flow ordering (ATGC)

| X | • | • | • | • |   |   |   |   |   |   |   |   |   |   |
|---|---|---|---|---|---|---|---|---|---|---|---|---|---|---|
|   | T | A | G | C | A | A | C | G | T | G | A | A | G | T |

| Y | • | • | • | • | • | • | • | • |   |   |   |   |   |   |
|---|---|---|---|---|---|---|---|---|---|---|---|---|---|---|
|   | T | A | G | C | A | A | C | G | T | G | A | A | G | T |

Cycle n+2 – conventional flow ordering (ATGC)

| X | • | • | • | • | • | • | • | • |   |   |   |   |   |   |
|---|---|---|---|---|---|---|---|---|---|---|---|---|---|---|
|   | T | A | G | C | A | A | C | G | T | G | A | A | G | T |

| Y | • | • | • | • | • | • | • | • | • | • |   |   |   |   |
|---|---|---|---|---|---|---|---|---|---|---|---|---|---|---|
|   | T | A | G | C | A | A | C | G | T | G | A | A | G | T |

Cycle n+3 – conventional flow ordering (ATGC)

| X | • | • | • | • | • | • | • | • | • | • |   |   |   |   |
|---|---|---|---|---|---|---|---|---|---|---|---|---|---|---|
|   | T | A | G | C | A | A | C | G | T | G | A | A | G | T |

| Y | • | • | • | • | • | • | • | • | • | • | • | • | • | • |
|---|---|---|---|---|---|---|---|---|---|---|---|---|---|---|
|   | T | A | G | C | A | A | C | G | T | G | A | A | G | T |

FIG. 4B

Cycle n – conventional flow ordering (ATGC) ─ 40

X | • | • | • |   |   |   |   |   |   |   |   |   |   |
  | T | A | G | C | A | A | C | G | T | G | A | A | G | G | T

Y | • | • | • | • |   |   |   |   |   |   |   |   |   |
  | T | A | G | C | A | A | C | G | T | G | A | A | G | G | T ─ 42

Cycle n+1 – alternate flow ordering (AGA-TCT-GAG-CTC)

X | • | • | • | • | • | • | • | • |   |   |   |   |   |
  | T | A | G | C | A | A | C | G | T | G | A | A | G | G | T

Y | • | • | • | • | • | • | • | • |   |   |   |   |   |
  | T | A | G | C | A | A | C | G | T | G | A | A | G | G | T

ALTERNATIVE NUCLEOTIDE FLOWS IN SEQUENCING-BY-SYNTHESIS METHODS

RELATED APPLICATIONS

This application is a divisional of U.S. application Ser. No. 13/689,252, filed on 29 Nov. 2012 (currently pending), which is a continuation of U.S. application Ser. No. 13/157, 865, filed on 10 Jun. 2011 (now abandoned), which claims the benefit of U.S. Provisional Application No. 61/354,173 filed on 11 Jun. 2010, which are all incorporated by reference herein.

TECHNICAL FIELD

The present teachings relate to nucleic acid sequencing, and more particularly, to the correction of errors that can arise in sequencing-by-synthesis techniques.

BACKGROUND

Several next-generation DNA sequencing approaches, often referred to as "sequencing-by-synthesis" approaches, use repeated cycles of primer extension with a DNA polymerase to generate a sequence of signals containing nucleotide sequence information of populations of template molecules. See, e.g., Hert et al, ELECTROPHORESIS, 29:4618-4626 (2008); Metzker, NATURE REVIEWS GENETICS, 11:31-46 (2010); Droege et al, J. BIOTECHNOLOGY, 136:3-10 (2008). A common problem in these approaches is the "dephasing" of primer extensions because of the accumulation of the cycle-to-cycle effects of incomplete extension and/or inappropriate extensions ("carry forward"), which lead to significant reductions in the signal-to-noise ratio as sequencing progresses. See, e.g., Ronaghi, GENOME RESEARCH, 11:3-11 (2001); Leamon et al, CHEMICAL REVIEWS, 107:3367-3376 (2007); Chen et al, International Patent Publication WO 2007/098049. Currently, such inefficiencies are dealt with by signal processing software, such as those described in Leamon et al. (cited above) and Chen et al. (cited above). But as longer read lengths and alternative detection schemes are sought, such as schemes for label-free extension detection (see, e.g., Rothberg et al, U.S. Patent Publication 2009/0127589), alternative methods for addressing signal loss from incomplete extension or carry forward errors would be highly desirable.

SUMMARY

In various embodiments, the present teachings apply to sequencing-by-synthesis techniques to sequence a template polynucleotide strand. To addresses the problem of incomplete extension (IE) and/or carry forward (CF) errors that can occur in sequencing-by-synthesis reactions, an alternative flow ordering of the nucleotides may be used. In various embodiments, alternative flow ordering may reduce and/or correct the loss of phasic synchrony in the population of template polynucleotide strands that result from IE and/or CF errors.

In one embodiment, the present teachings provide a method of sequencing a polynucleotide strand, comprising: (a) providing the polynucleotide strand with a primer annealed thereto and a polymerase operably bound to the polynucleotide strand; and (b) successively exposing the polynucleotide strand to the flow of four different dNTPs according to a predetermined ordering, wherein the predetermined ordering comprises an alternate ordering which is not a continuous repeat of an ordering of the four different dNTPs.

In another embodiment, the present teachings provide an apparatus for sequencing a polynucleotide strand, comprising: (a) a flow chamber for receiving flows of different dNTP reagents; (b) multiple reservoirs that each contain a different dNTP reagent; (c) flow paths from each of the reservoirs to the flow chamber; and (d) a fluidics controller that controls the flow from the reservoirs to the flow chamber, wherein the fluidics controller is programmed to successively provide flow from the multiple reservoirs to the flow chamber according to a predetermined ordering, wherein the predetermined ordering comprises an alternate ordering which is not a continuous repeat of an ordering of the four different dNTP reagent flows.

In another embodiment, the present teachings provide a method of performing template-based extension of a primer, comprising: providing at least one template polynucleotide strand having a primer and polymerase operably bound thereto; and successively exposing the template polynucleotide strand to a plurality of each kind of flow such that (a) a flow of one kind is always followed by a flow of a different kind; and (b) at least one flow of each kind is followed by a flow of the same kind after a single intervening flow of a different kind.

In another embodiment, the present teachings provide a method of determining the sequence of a template polynucleotide strand by template-based extension of a primer, comprising: (a) delivering a known nucleoside triphosphate precursor to a template-based primer extension reaction of a polynucleotide strand, the known nucleoside triphosphate precursor being delivered according to a predetermined ordering of dNTP flows; (b) detecting incorporation of the known nucleoside triphosphate whenever its complement is present in the template polynucleotide strand adjacent to the primer; and (c) repeating steps (a) and (b) until the sequence of the template polynucleotide strand is determined; wherein the predetermined ordering of dNTP flows is defined by (i) a flow of one kind is always followed by a flow of a different kind; and (ii) at least one flow of each kind is followed by a flow of the same kind after a single intervening flow of a different kind.

In another embodiment, the present teachings provide a method for sequencing a template polynucleotide strand comprising: (a) disposing a plurality of template polynucleotide strands into a plurality of reaction chambers, each reaction chamber comprising a template polynucleotide strand having a sequencing primer hybridized thereto and a polymerase operably bound thereto; (b) introducing a known nucleoside triphosphates into each reaction chamber according to a predetermined ordering of dNTP flows; (c) detecting sequential incorporation at the 3' end of the sequencing primer of one or more nucleoside triphosphates if the known nucleoside triphosphate is complementary to corresponding nucleotides in the template nucleic acid; (d) washing away unincorporated nucleoside triphosphates from the reaction chamber; and (e) repeating steps (b) through (d) until the polynucleotide strand is sequenced; wherein the predetermined ordering of dNTP flows is defined by (i) a flow of one kind is always followed by a flow of a different kind; and (iii) at least one flow of each kind is followed by a flow of the same kind after a single intervening flow of a different kind.

In another embodiment, the present teachings provide a method of sequencing a polynucleotide strand, comprising: providing the polynucleotide strand with a primer annealed thereto and a polymerase operably bound to the polynucleotide strand; successively exposing the polynucleotide strand to the flow of four different dNTPs according to a first predetermined ordering; and successively exposing the polynucleotide strand to the flow of four different dNTPs according to a second predetermined ordering, wherein the second predetermined ordering is different from the first predetermined ordering.

BRIEF DESCRIPTIONS OF THE DRAWINGS

FIG. 2 discloses SEQ ID NO: 1.

FIGS. 3A and 3B show an exemplary alternate flow ordering that may be used to improve phasic synchrony in a population of template polynucleotide strands. FIGS. 3A and 3B disclose SEQ ID NO: 1.

FIGS. 4A and 4B show an exemplary alternate flow ordering that may be used to improve phasic synchrony in a population of template polynucleotide strands. FIGS. 4A and 4B disclose SEQ ID NO: 2.

DETAILED DESCRIPTION

Figure 1:
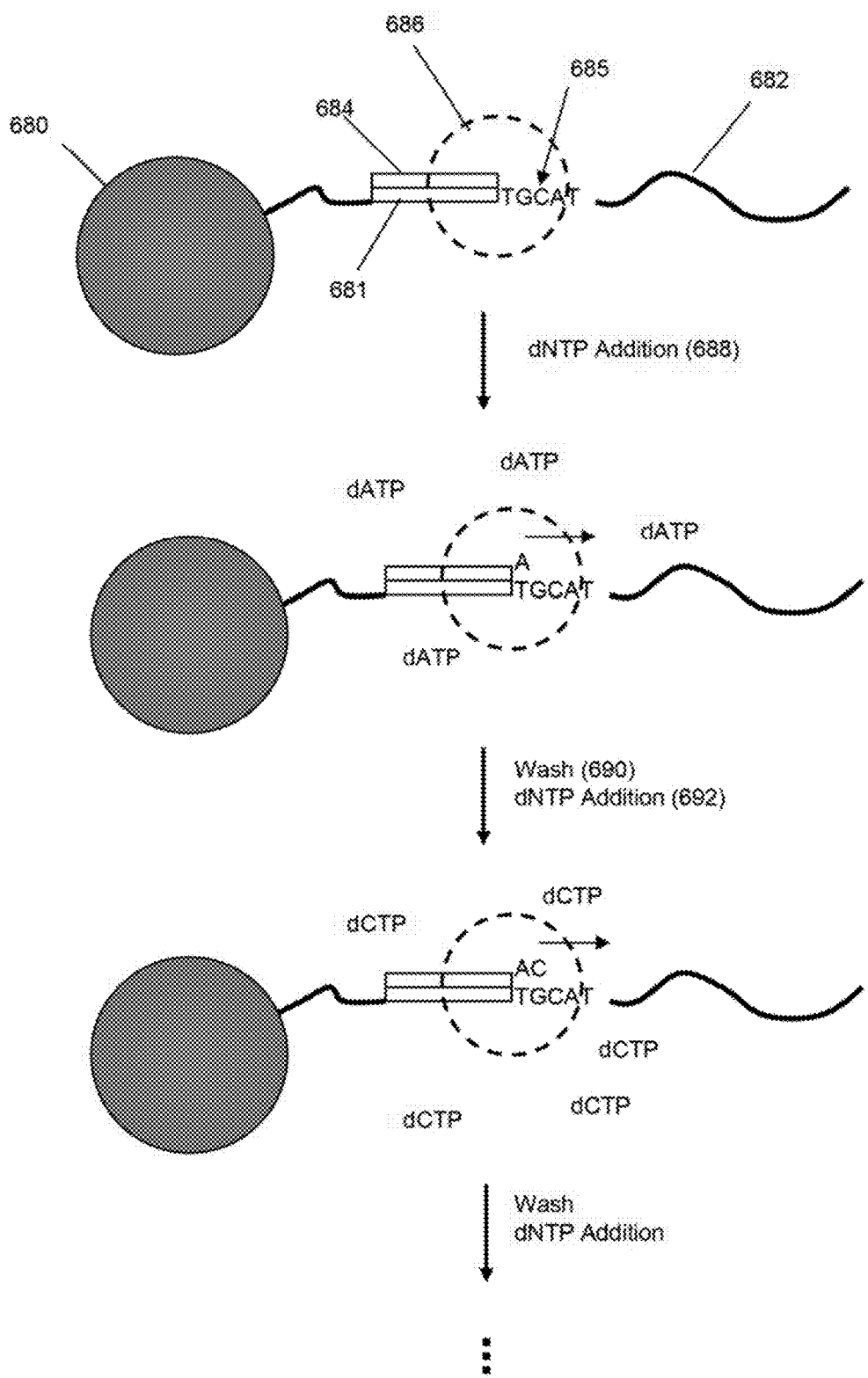
FIG. 1 shows an exemplary sequencing-by-synthesis process.

The practice of the present teachings may employ, unless otherwise indicated, conventional techniques and descriptions of organic chemistry, molecular biology (including recombinant techniques), cell biology, and biochemistry. Such conventional techniques include, but are not limited to, preparation of synthetic polynucleotides, polymerization techniques, chemical and physical analysis of polymer particles, nucleic acid sequencing and analysis, and the like. Specific illustrations of suitable techniques are given in the examples below. However, other equivalent conventional procedures can also be used. Such conventional techniques and descriptions can be found in standard laboratory manuals such as
GENOME ANALYSIS: A LABORATORY MANUAL SERIES (vols. I-IV); PCR PRIMER: A LABORATORY MANUAL;
MOLECULAR CLONING: A LABORATORY MANUAL (all from Cold Spring Harbor Laboratory Press); Hermanson, BIOCONJUGATE TECHNIQUES, 2nd ed. (Academic Press, 2008); and the like.

Sequencing-by-Synthesis

The present teachings apply sequencing-by-synthesis techniques to sequence a template polynucleotide strand. In general, sequencing-by-synthesis (SBS) may refer to methods for determining the nucleotide sequence of a target polynucleotide by a polymerase extension reaction. In various embodiments, the process sequences one or more template polynucleotide strands, which may be provided in any suitable manner. In some embodiments, the template strands may be coupled to or associated with a support, such as a microparticle, bead, or the like, and are loaded into reaction chambers. In other embodiments, the template polynucleotide strands may be associated with a substrate surface or present in a liquid phase with or without being coupled to a support. For example, templates may be prepared as described in U.S. Pat. No. 7,323,305, which is incorporated by reference.

During a typical sequencing reaction, a primer is annealed to the template polynucleotide strand to form a primer-template duplex, and a polymerase is operably bound to the primer-template duplex so that it is capable of incorporating a nucleotide onto the 3' end of the primer. As used herein, "operably bound" may refer to the primer being annealed to a template strand so that the primer's 3' end may be extended by a polymerase and that a polymerase is bound to the primer-template duplex, or in close proximity thereof, so that extension can take place when dNTPs are flowed. The primer-template-polymerase complex is subjected to repeated exposures of different nucleotides. If a nucleotide(s) is incorporated, then the signal resulting from the incorporation reaction is detected. A wash step may be performed to remove unincorporated nucleotides prior to the next nucleotide exposure. After repeated cycles of nucleotide addition, primer extension, and signal acquisition, the nucleotide sequence of the template strand may be determined.

The present teachings may use any of a variety of sequencing techniques and is particularly suitable for sequencing-by-synthesis techniques. Examples of such techniques are described in the literature, including the following, which are incorporated by reference: Rothberg et al, U.S. Patent Publication 2009/0026082; Anderson et al, SENSORS AND ACTUATORS B CHEM., 129:79-86 (2008); Pourmand et al, PROC. NATL. ACAD. SCI., 103:6466-6470 (2006). Variants of sequencing-by-synthesis techniques include methods where the nucleotides are modified to be reversible terminators (sometimes referred to as cyclic reversible termination (CRT) methods, as described in Metzker (cited above)) and methods where the nucleotides are unmodified (sometimes referred to as cyclic single base delivery (CSD) methods). The incorporation reaction generates or results in a product or constituent with a property capable of being monitored and used to detect the incorporation event. Non-limiting examples of such properties that may be associated with incorporation reactions include changes in magnitude (e.g., heat) or concentration (e.g., pyrophosphate and/or hydrogen ions), and signal (e.g., fluorescence, chemiluminescence, light generation). In the various approaches, the amount of the detected product or constituent may be monotonically related to the number of nucleotides incorporated. Non-limiting examples of suitable sequencing chemistries include that used on the Genome Analyzer/HiSeq/MiSeq platforms (Illumina, Inc.; See, e.g., Balasubramanian, U.S. Pat. Nos. 6,833,246 and 5,750,341); those applying pyrosequencing-based sequencing methods such as that used by Roche/454 Technologies on the GS FLX, GS FLX Titanium, and GS Junior platforms (see, e.g., Ronaghi et al, SCIENCE, 281: 363 (1998); and Maguiles et al (cited above)); and those by Life Technologies/Ion Torrent in the PGM system (see, e.g., US 2010/0137143 and US 2009/0026082).

In an exemplary conventional SBS method, the four nucleotides are sequentially and repeatedly delivered (flowed) in the same order. For example, the first nucleotide delivered may be dATP, then dCTP, then dGTP, then dTTP (or a permutation thereof), after which this sequence is repeated. Such deliveries of nucleotides to a reaction vessel or chamber may be referred to as "flows" of nucleotide triphosphates (or dNTPs). For convenience, a flow of dATP will sometimes be referred to as "a flow of A" or "an A flow," and a sequence of flows may be represented as a sequence of letters, such as "ATGT" indicating "a flow of dATP, followed by a flow of dTTP, followed by a flow of dGTP, followed by a flow of dTTP." In each flow step of the cycle, the polymerase may generally extend the primer by incorporating the flowed dNTP where the next base in the template strand is the complement of the flowed dNTP. Thus, if there is one complementary base, then one base or dNTP incorporation is expected; if two complementary bases, then two incorporations are expected; if three complementary bases, then three incorporations are expected, and so on.

The present teachings may use any of various techniques for detecting the nucleotide incorporation(s). For example, some sequencing-by-synthesis techniques provide for the detection of pyrophosphate (PPi) released by the incorporation reaction (see, e.g., U.S. Pat. Nos. 6,210,891; 6,258,568; and 6,828,100). In another example, some sequencing-by-synthesis techniques may detect labels associated with the nucleotides, such as mass tags, fluorescent, and/or chemiluminescent labels. Where detectable labels are used, an inactivation step may be included in the workflow (e.g., by chemical cleavage or photobleaching) prior to the next cycle of synthesis and detection.

In certain embodiments, the present teachings may use a pH-based method of detecting nucleotide incorporation(s). Such an approach may detect hydrogen ions released from the polymerase-catalyzed extension reactions in the absence of a specific label or tag. The hydrogen ions released by a population of template strands undergoing the base incorporation(s) will change the local pH of the reaction chamber, which can be detected. Thus, in pH-based methods for DNA sequencing, base incorporations are determined by measuring these hydrogen ions that are generated. Additional details of pH-based sequence detection systems and methods may be found in commonly-assigned U.S. Patent Application Publication No. 2009/0127589 and No. 2009/0026082, which are incorporated by reference. While the examples below are discussed in connection with pH-based sequence detection, it will be appreciated that the present teachings may be readily adapted to other sequencing approaches such as the exemplary technologies mentioned above including pyro-sequencing. Such approaches can likewise benefit from the phase correction, signal enhancement, improved accuracy and noise reduction features of the alternative nucleotide flows approaches described herein and are understood to be within the scope of the present teachings.

It will be appreciated that in connection with pH-based detection methods, the production of hydrogen ions may be monotonically related to the number of contiguous complementary bases in the template strands (as well as the total number of template molecules with primer and polymerase that participate in an extension reaction). Thus, when there is a number of contiguous identical complementary bases in the template (i.e., a homopolymer region), the number of hydrogen ions generated, and therefore the magnitude of the local pH change, is generally proportional to the number of contiguous identical complementary bases. (The corresponding output signals may sometimes be referred to as "1-mer", "2-mer", "3-mer" output signals, and so on, based on the expected number of repetitive bases). Where the next base in the template is not complementary to the flowed dNTP, generally no incorporation occurs and there is no substantial release of hydrogen ions (in which case, the output signal is sometimes referred to as a "0-mer" output signal).

In each wash step of the cycle, a wash solution (typically having a predetermined pH) is used to remove residual dNTP of the previous step in order to prevent misincorporations in later cycles. Usually, the four different kinds of dNTP are flowed sequentially to the reaction chambers, so that each reaction is exposed to one of the four different dNTPs for a given flow, such as in the following sequence: dATP, dCTP, dGTP, dTTP, dATP, dCTP, dGTP, dTTP, and so on, with the exposure, incorporation, and detection steps followed by a wash step. An example of this process is illustrated in FIG. 1, which shows a template strand 682 attached to a particle 680. Primer 684 is annealed to template strand 682 at its primer binding site 681. A DNA polymerase 686 is operably bound to the template-primer duplex. Template strand 682 has the sequence 685, which is awaiting complementary base incorporation. Upon the flow of dNTP (shown as dATP), polymerase 686 incorporates a nucleotide since "T" is the next nucleotide in template strand 682 (because the "T" base is complementary to the flowed dATP nucleotide). Wash step 690 follows, after which the next dNTP (dCTP) is flowed 692. Optionally, after each step of flowing a dNTP, the reaction chambers may be treated with a dNTP-destroying agent (such as apyrase) to eliminate any residual dNTPs remaining in the chamber, which can cause spurious extensions in subsequent cycles.

Figure 2:
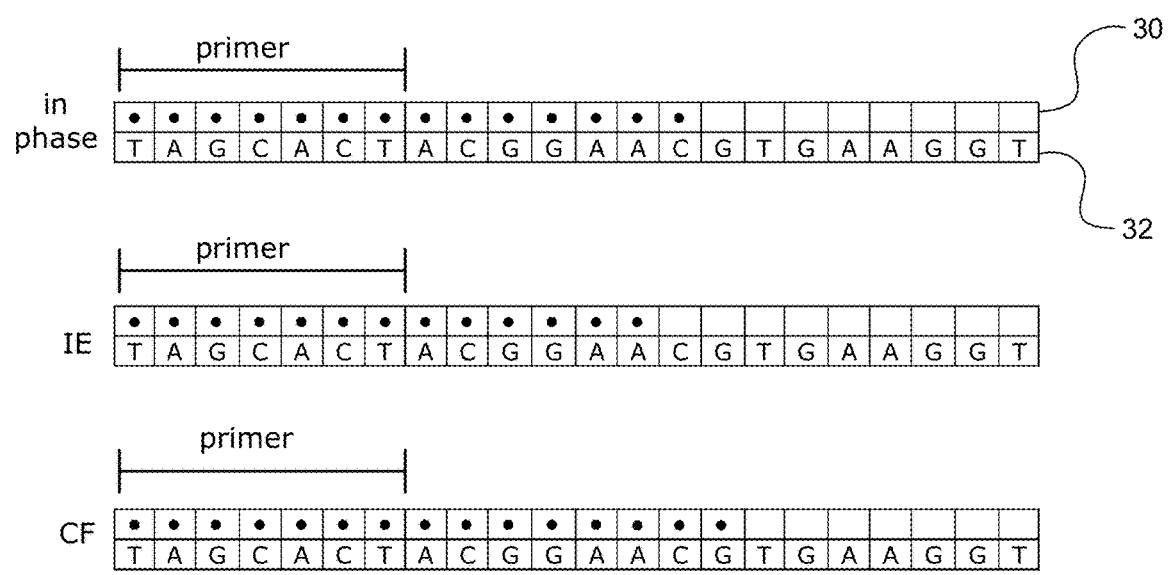
FIG. 2 shows examples of IE and CF errors that may occur during sequencing.

FIG. 2 shows an example of IE and CF errors. FIG. 2 shows three DNA duplexes. For each duplex, the bottom row of boxes represents the template polynucleotide strand 32 and the top row of boxes represents the complementary extension strand 30 being extended by the polymerase. The extension strand includes the primer portion, as indicated by the bar. In this figure, the (•)-filled boxes indicate the incorporation of complementary nucleotides.

The top DNA duplex (labeled "in-phase") represents members of the population that are in the correct phase, i.e., in-phase. The middle DNA duplex (labeled "IE") represents a portion of the population that has experienced an exemplary omission at the C nucleotide, i.e., an incomplete extension error causing dephasing of the population. The bottom DNA duplex (labeled "CF") represents a portion of the population that has experienced an exemplary erroneous incorporation at the G nucleotide, i.e., a carry forward error causing dephasing of the population.

Alternate Flow Orderings

The present teachings address the problem of incomplete extension (IE) and/or carry forward (CF) occurrences in sequencing reactions by using an alternative (non-sequential) ordering for delivering nucleotides. This alternative ordering may reduce and/or correct the loss of phasic synchrony in the population of template polynucleotide strands that result from IE and/or CF occurrences. As used herein, an "alternative ordering" of dNTP flows means that the ordering is not a continuous repeat of an ordering of the four different dNTPs. In other words, in an alternate flow ordering, the dNTPs are flowed in an order that is not a contiguous, sequential repetition of the same 4-member units, each 4-member unit being a sequence of the four different dNTPs. This alternate flow ordering represents at least some portion of the sequencing run.

The alternate flow ordering may be reflected in the overall predetermined flow ordering in any of various ways. In some embodiments, the alternate flow ordering constitutes one or more parts of the overall predetermined ordering, with one or more other parts of the overall predetermined ordering using a conventional flow ordering (i.e., not an alternate flow ordering). For example, the alternate flow ordering may be used intermittently with a conventional flow ordering. In some embodiments, the overall predetermined ordering consists of only the alternate flow ordering throughout the sequencing run. In some embodiments, the method may be implemented with real-time detection of CF and/or IE errors and applying the alternate flow ordering in response to the error detection. For example, the alternate flow ordering may be used when the CF and/or IE errors reach a certain threshold level. In some embodiments, the alternate flow orderings may be used according to the position in the sequence read. For example, the alternate flow ordering may be used after a certain read length of the sequence or used more frequently at later stages of the sequence read. This may be useful in instances where the CF and/or IE errors increase at later stages of the read or in longer reads.

In some cases, the overall predetermined ordering comprises a first predetermined ordering for the flow of four different dNTPs and a second predetermined ordering for the flow of the four different dNTPs, with the second predetermined ordering being different from the first predetermined ordering. For example, the first predetermined ordering may be a conventional flow ordering and the second predetermined ordering may be an alternate flow order.

In certain embodiments, the present teachings may be directed to any sequencing method (including SBS methods) where delivery of dNTPs to a reaction is not a continuous repetition of the same initial ordering of flows of the four dNTPs, such as: ACGT-ACGT-ACGT- . . . and so on. Such an initial ordering of dNTP flows may be any permutation of ACGT, such as ACTG, TGCA, and so on. The alternate flow ordering may be implemented in a variety of different ways. In certain embodiments of the present teachings, the dNTPs are delivered in a predetermined ordering that comprises an alternate ordering where (a) a flow of one kind is always followed by a flow of a different kind; and (b) at least one flow of each kind is followed by a flow of the same kind after a single intervening flow of a different kind. In some cases, the number of flows of each kind in the alternative ordering is the same.

If "N" is used to represent the flow of any one of dATP, dCTP, dGTP, or dTTP, then in one example, the predetermined ordering of dNTP flows can include the following subsequence: N-W-N for each dNTP N, where W is any dNTP not N. In another example, the ordering of dNTP flows can include an alternate ordering with the following subsequence: N-W-N-Z for each dNTP N, where W is any dNTP not N, and Z is any dNTP that is neither N nor W. Flow orderings of the present teachings may have a variety of lengths, which are the total number of flows making up a predetermined ordering. In some cases, the lengths of the flow orderings may be provided in subsets comprising a multiple of defined base flows. For example, the length of the flow orderings in the present teachings may be any multiple of four, eight, or other multiples. An exemplary 8-flow ordering of the present teachings is AT-AC-GC-GT, where the "GC-G" subsequence (representing a N-W-N sequence) is present. Note also that there is a "T-AT" subsequence (representing a N-W-N sequence) when the 8-flow ordering is contiguously repeated. In certain embodiments, alternate flow orderings of the present teachings have a length selected from the group consisting of 8, 12, 16, 20, 24, 28 and 32. However, it will be appreciated that other flow ordering lengths may be used. Exemplary alternate flow orderings of 12 flows are TCT-AGA-CTC-GAG and ACA-CGC-GTG-TAT. An exemplary alternate flow ordering of 20 flows is TACAT-ACGCA-CGTGC-GTATG, which may be repeated one or more times (in part or whole) to sequence a desired template length.

In another embodiment, the alternate flow ordering includes a first dNTP flow, a second dNTP flow, a third dNTP flow, and a fourth dNTP flow, with each flow being a different dNTP; wherein the fourth dNTP flow does not occur until at least one of the first, second, or third dNTP flows are repeated at least once. For example, for the exemplary 8-flow ordering of AT-AC-GC-GT given above, the G nucleotide is not flowed until each of A, T, and C are flowed, with A being flowed twice. Likewise, for the exemplary 12-flow ordering of ACA-CGC-GTG-TAT, the T nucleotide is not flowed until each of A, C, and G are flowed (with A being flowed twice, C being flowed three times, and G being flowed twice). In some cases, the number of flows for each of the four different dNTPs in the alternate flow ordering is the same. For example, for the exemplary 8-flow ordering of AT-AC-GC-GT given above, each of the four nucleotides are flowed twice. Likewise, for the exemplary 12-flow ordering of TCT-AGA-CTC-GAG and ACA-CGC-GTG-TAT given above, each of the four nucleotides are flowed three times.

In various embodiments, the inclusion or removal of any flow of a selected nucleotide from a series of flows of a sequencing run may be used to impart an alternative flow ordering according to the present teachings. The number and/or type of flow may, for example, be as few as a single added base flow over the course of the sequencing run (or removal of a selected base flow). As described above, imparting a non-sequential four base flow ordering (e.g., not strictly GATC, GATC, . . . over the entire sequencing run) may provide for improved sequencing quality and/or signal detection by reducing IE and/or CF effects.

The flow of dNTPs can be provided in any suitable manner, including delivery by pipettes, or through tubes or passages connected to a flow chamber. The duration, concentration, and/or other flow parameters may be the same or different for each dNTP flow. Likewise, the duration, composition, and/or concentration for each wash flow may be the same or different.

FIGS. 3A and 3B show an example of how the alternate flow ordering of the present teachings can be used to improve phasic synchrony. FIG. 3A shows a partial view of two exemplary duplexes A and B, each with a polynucleotide template strand 36 and an extension strand 34. This view may represent part of a population of template strands that are being subjected to a series of flow cycles during a sequencing run. For each duplex, the bottom row of boxes represents the template strand 36 and the top row of boxes represents the complementary extension strand 34 hybridized to the template strand and being extended by the polymerase. In the figure, the (•)-filled boxes indicate the incorporation of complementary nucleotides in a growing extension strand.

In this example, both templates A and B are represented as having already undergone n cycles of a representative conventional, repeated ATGC flow ordering pattern, i.e., ATGC-ATGC-ATGC- . . . . FIG. 3A depicts only a representative portion of the template/extension strand duplex for cycles n through n+3. During cycle n, the template strand B is exemplified with an omitted incorporation at the nucleotide base A (marked by the "x"). This may reflect an incomplete extension error in template strand B, such that the extension strand is out-of-phase with that of the template strand A. FIG. 3A shows the extension strand continuing to be extended through further cycles n+1, n+2, and n+3 of the repeating ATGC flow ordering. As seen here, after multiple further cycles, the extension strand on template strand B (with the IE error) continues to lag behind the in-phase template strand A. This representation of an IE occurrence is only one example and it will be appreciated that many different IE occurrences are possible and can be introduced at any point during a sequencing run. Moreover, different template strands may experience different IE occurrences and a single template strand may have multiple IE occurrences at different positions.

FIG. 3B shows the same pair of template strands A and B as in FIG. 3A, also with the same IE error at the location marked "x". Also, as in FIG. 3A, the templates strands have been subjected to n cycles of the conventional repeating ATGC flow ordering. However, from cycles n+1 to n+3, the flow ordering is changed to the alternate flow ordering of AGA-TCT-GAG-CTC. As seen here, after the third cycle of the alternate flow ordering, template strand B (with the IE error) has been resynchronized to the in-phase template strand A.

FIGS. 4A and 4B show another example of how the alternate flow ordering of the present teachings can be used to improve phasic synchrony in the population of template polynucleotide strands. FIG. 4A shows a partial view of two exemplary duplexes X and Y, each with a polynucleotide template strand 42 and an extension strand 40. For each duplex, the bottom row of boxes represents the template strand 42 and the top row of boxes represents the complementary extension strand 40 being extended by the polymerase. In this figure, the (•)-filled boxes indicate the incorporation of complementary nucleotides.

In this example, both templates X and Y have already undergone n cycles of a conventional, repeated ATGC flow ordering pattern, i.e., ATGC-ATGC-ATGC- . . . . FIG. 4A depicts a representative portion of the template/extension strand duplex for cycles n through n+3. During cycle n, the template strand Y experiences an erroneous additional incorporation at the nucleotide base C. This may reflect a carry forward error in template strand Y such that the extension strand is out-of-phase with that of the template strand X. FIG. 4A shows the extension strand continuing to be extended through further cycles n+1, n+2, and n+3 of the repeating ATGC flow ordering. As seen here, after multiple further cycles, the extension strand on template strand Y (with the CF error) continues to be ahead of the in-phase template strand X. This representation of a CF occurrence is only one example and it will be appreciated that many different CF occurrences are possible and can be introduced at any point during a sequencing run. Moreover, different template strands may experience different CF occurrences and a single template strand may have multiple CF occurrences at different positions.

FIG. 4B shows the same pair of template strands X and Y as in FIG. 4A, also with the same CF error in template strand Y. Also, as in FIG. 4A, the templates strands have been subjected to n cycles of the conventional repeating ATGC flow pattern. However, from cycles n+1 to n+3, the flow pattern is changed to the alternate flow ordering of AGA-TCT-GAG-CTC. As seen here, after a single cycle of the alternate flow ordering, template strand Y (with the CF error) has been resynchronized to the in-phase template strand X.

It will be appreciated that achieving or improving phasic synchrony desirably enhances the ability to identify nucleotide incorporations and correctly ascertain the sequence of templates undergoing analysis. In many sequencing applications, dephasing issues may be relatively small early in the sequencing run; however, their effects may accumulate as the sequencing progresses and result in degraded sequencing quality when longer templates are used. From a practical perspective, it will be appreciated that the corrective effect of the alternate flow ordering will desirably enhance the base calling abilities of a sequencing instrument by reducing or eliminating spurious signals associated with out-of-phase templates.

In various embodiments, alternate nucleotide flows can be included within or in connection with a series of sequencing flows as a mechanism by which to counteract the accumulated dephasing of templates. Such alternate flows may therefore be used in some embodiments not to completely remove or alleviate dephasing, but rather as a mechanism to balance or reduce accumulated dephasing effects while at the same time maintaining an efficient or desirable number of flows to achieve a selected/expected throughout (e.g., the flows used to sequence a respective template length). Use of the present teachings for sequencing may result in a reduction or correction of CF and/or IE effects, improvement in phasic synchrony, increased signal-to-noise ratio, and/or improved base calling accuracy.

Figure 7:
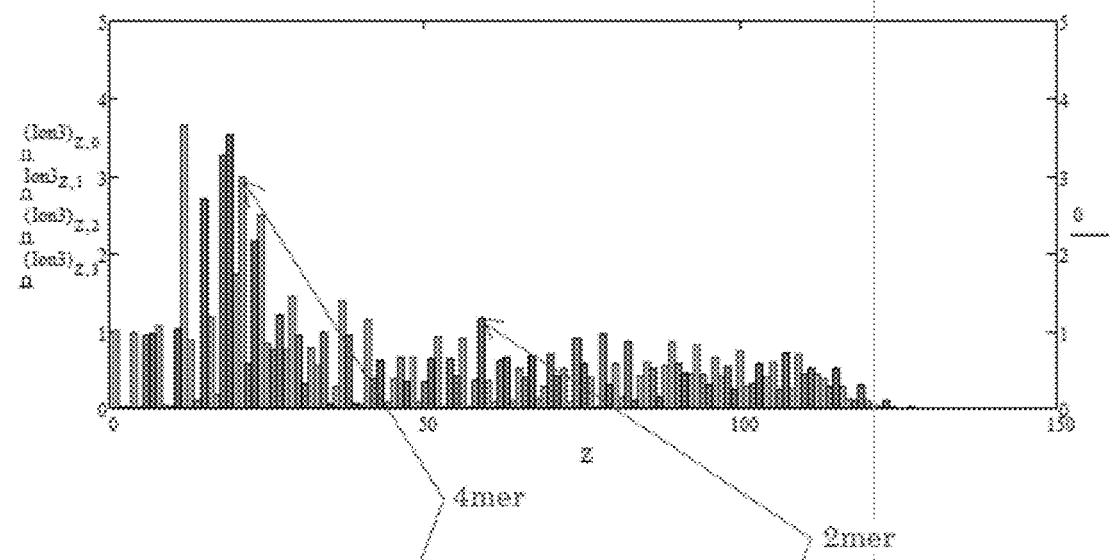
FIG. 7 shows sample ionograms from a sequencing simulation of a test fragment.
Figure 7:
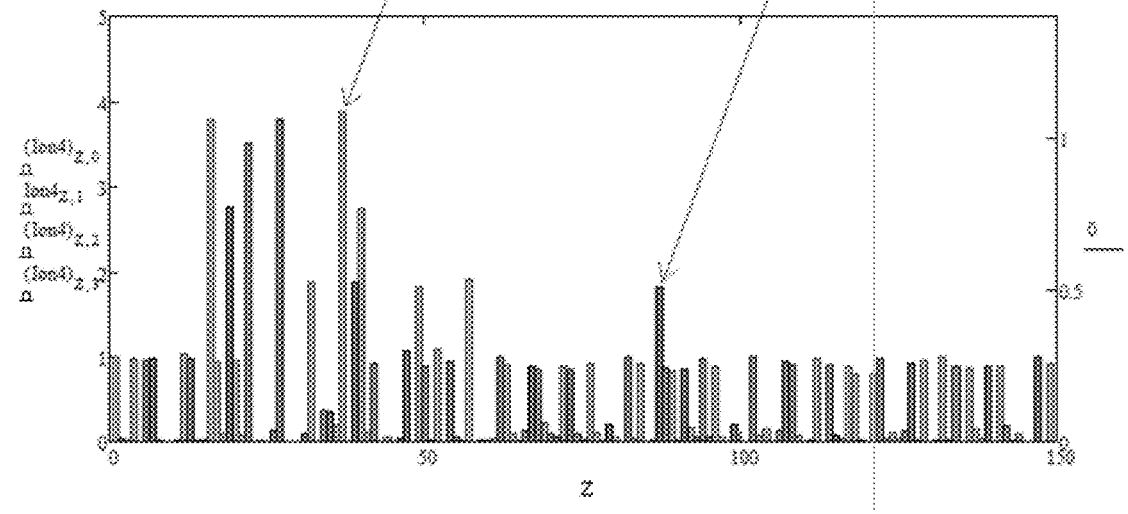

FIG. 7 shows two ionograms from a simulation of a pH-based sequencing run for a particular test fragment using 1% as the error rate parameters for both CF and IE errors. The ionogram in the upper panel shows the signal peaks acquired using a conventional TACG flow order. The ionogram in the lower panel shows the signal peaks acquired using an alternate flow ordering of TACATACGCACGT-GCGTATG. The labeled arrows point to two example incorporation signals at the same sequence position on the test fragment. The "4-mer" arrows point to the signals from the same 4-mer homopolymer subsequence of the test fragment. The "2-mer" arrows point to the signals from the same 2-mer homopolymer subsequence of the test fragment. As seen here, the ionogram in the lower panel (using the alternate flow ordering) has signals that more clearly define the base-calling classifications as being 4-mer and 2-mer, as well the base-calling classifications for other signals in the test fragment.

Sequencing Instrumentation

Instruments for delivering reagents for multistep sequencing processes are known, and typically comprise reservoirs for reagents, one or more reaction chambers or areas, and fluidics under computer control for selecting and delivering the various reagents including dNTPs to the one or more reaction chambers or areas. Exemplary instrument systems for carrying out massively parallel SBS reactions with electronic detection are disclosed in Rothberg et al, U.S. Patent Publication No. 2009/0127589 and No. 2009/0026082; and Rothberg et al, U.K. Patent Application GB2461127. Likewise, conventional fluorescence-based SBS sequencing instrumentation are disclosed in Rothberg et al, U.S. Pat. Nos. 7,211,390; 7,244,559; and 7,264,929. In fluorescence-based SBS sequencing instrumentation, the release of inorganic pyrophosphate from an incorporation reaction initiates an enzyme cascade that results in light emission, which is then detected by the instrument. The alternate flow orderings of the present teachings can be used with these and other sequencing methods and systems.

Figure 5:
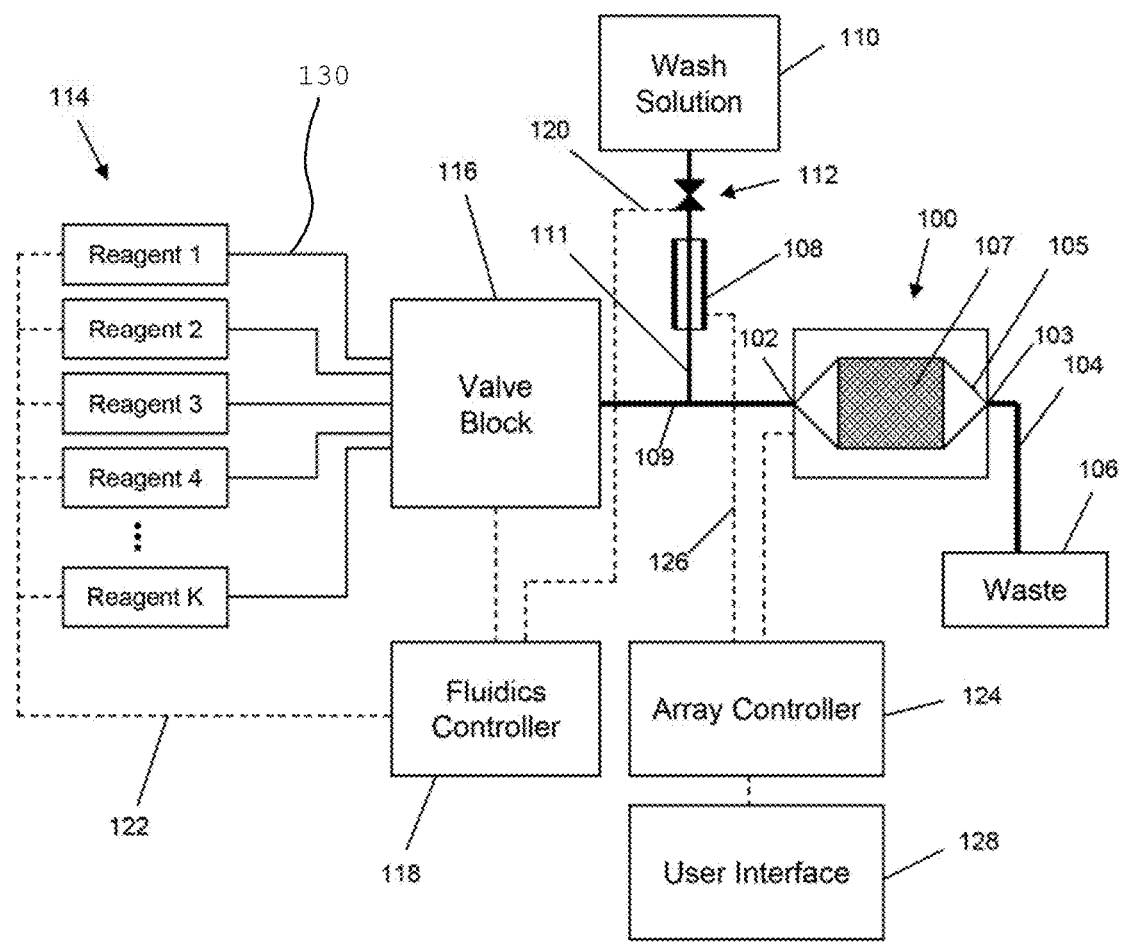
FIG. 5 is a diagram showing a sequencing apparatus according to an embodiment of the present teachings.

The present teachings also provide an apparatus for sequencing template polynucleotide strands according to the method of the present teachings. A particular example of an apparatus of the present teachings is shown in FIG. 5. The apparatus of FIG. 5 is configured for pH-based sequencing and includes multiple reservoirs for containing reagents 1 through K (114). These reagents contain the dNTPs to be flowed for the SBS process. The reagents 114 are flowed through fluid passages 130 and through a valve block 116 that controls the flow of the reagents to flow chamber 105 (also referred to herein as a reaction chamber) via fluid passage 109. The apparatus includes a reservoir 110 for containing a wash solution that is used to wash away the dNTP reagent of the previous step. Reagents are discarded through waste passage 104 into a waste container 106 after exiting the flow chamber 105.

The apparatus also includes a fluidics controller 118, which may programmed to control the flow from the multiple reagent reservoirs to the flow chamber according to a predetermined ordering that comprises an alternate flow ordering, as described above. For this purpose, fluidics controller 118 may be programmed to cause the flow of reagents 114 from the reagents reservoir and operate the valves 112 and 116. The fluidics controller may use any conventional instrument control software, such as LabView (National Instruments, Austin, Tex.). The reagents may be driven through the fluid pathways 130, valves, and flow cell by any conventional mechanism such as pumps or gas pressure.

The apparatus also has a valve 112 for controlling the flow of wash solution into passage 109. When valve 112 is closed, the flow of wash solution is stopped, but there is still uninterrupted fluid and electrical communication between reference electrode 108, passage 109, and sensor array 100. Some of the reagent flowing through passage 109 may diffuse into passage 111, but the distance between reference electrode 108 and the junction between passages 109 and 111 is selected so that little or no amount of the reagents flowing in common passage 109 reach reference electrode 108. This configuration has the advantage of ensuring that reference electrode 108 is in contact with only a single fluid or reagent throughout an entire multi-step reaction process. Reference electrode 108 may be constructed in any suitable fashion. In this particular embodiment, reference electrode 108 is a tube made of a conductive material which forms part of passage 111. Although FIG. 5 shows the reference electrode 108 as a cylinder that is concentric with the flow path (to represent the preferred configuration in which a tube of conductive material encloses part of a flow path), other embodiments may use any suitable configuration for a reference electrode in a flow path.

As shown in FIG. 5, flow chamber 105 is loaded with a flow cell that includes an inlet 102, an outlet 103, and a microwell array 107 which is operationally associated with a sensor array 100 that measures physical and/or chemical parameters in the microwells that provide information about the status of a reaction taking place therein; or in the case of empty wells, information about the physical and/or chemical environment in the flow cell. Each microwell may have a sensor for detecting an analyte or reaction property of interest. In this particular embodiment, the microwell array is integrated with the sensor array as a single chip, as explained more fully below. A flow cell can have a variety of designs for controlling the path and flow rate of reagents over the microwell array. In some embodiments, a flow cell is a microfluidics device, which may be fabricated with micromachining techniques or precision molding to include additional fluidic passages, chambers, and so on. This particular apparatus has an array controller 126 which receives information from sensor array 100 and reference electrode 108 via communication line 126. A user interface 128 provides an interface through which a user may interact with the apparatus.

Figure 6:
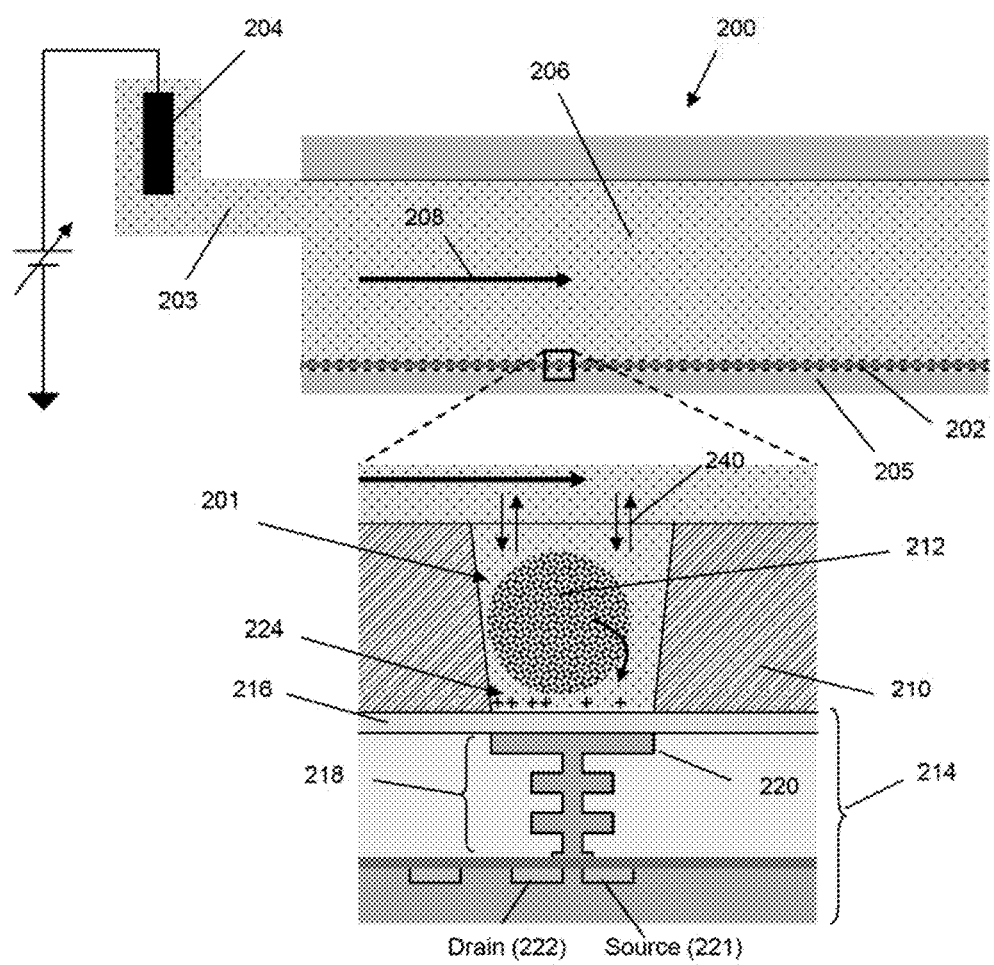
FIG. 6 shows a close-up, cross-sectional view of a flow cell according to an embodiment of the present teachings.

FIG. 6 is an expanded and cross-sectional view of flow cell 200 showing a portion of a flow chamber 206 with reagent flow 208 moving across the surface of microwell array 202 over the open ends of the microwells. Preferably, microwell array 202 and sensor array 205 together form an integrated unit forming a bottom wall or floor of flow cell 200. In one embodiment, reference electrode 204 is fluidly connected to flow chamber 206. A microwell 201 and sensor 214 are shown in an expanded view. Microwell 201 is formed in the bulk material 210 by any conventional microfabrication technique. The volume, shape, aspect ratio (such as base width-to-well depth ratio), and other dimensional characteristics of the microwells are design choices that depend on a particular application, including the nature of the reaction taking place, as well as the reagents, byproducts, and labeling techniques (if any) that are employed. Sensor 214 is a chemFET with a floating gate 218 having sensor plate 220 separated from the microwell interior by passivation layer 216. Sensor 214 is predominantly responsive to (and generates an output signal related to) the amount of charge 224 present on the passivation layer 216 opposite of sensor plate 220. Changes in charge 224 cause changes in the current between source 221 and drain 222 of the FET, which may be used directly to provide a current-based output signal or indirectly with additional circuitry to provide a voltage-based output signal. Reactants, wash solutions, and other reagents move into microwells from flow chamber 206 primarily by diffusion 240.

In another embodiment of the present teaching, a fluidics controller (e.g., fluidics controller 118 in FIG. 5) is programmed to cause the flow of dNTP reagents in the manner described above. Another embodiment of the present teachings includes a computer-readable storage medium having executable instructions for performing the sequencing methods described above. The storage medium may be any type of computer-readable medium (i.e., one capable of being read by a computer), including non-transitory storage mediums such as magnetic or optical tape or disks (e.g., hard disk or CD-ROM), solid state volatile or non-volatile memory, including random access memory (RAM), read-only memory (ROM), electronically programmable memory (EPROM or EEPROM), or flash memory. The term "non-transitory computer-readable storage medium" encompasses all computer-readable storage media, but excludes a transitory, propagating signal. As explained above, the instructions on the computer-readable storage medium may control the operation of a fluidics controller or sequencing apparatus of the present teachings.

Terminology

Unless otherwise specifically designated herein, terms and symbols of nucleic acid chemistry, biochemistry, genetics, and molecular biology used herein follow those of standard treatises and texts in the field. See, for example, Kornberg and Baker, DNA REPLICATION, 2nd ed. (W.H. Freeman, New York, 1992); Lehninger, BIOCHEMISTRY, 2nd ed. (Worth Publishers, New York, 1975); Strachan and Read, HUMAN MOLECULAR GENETICS, 2nd ed. (Wiley-Less, New York, 1999).

"Microwell," which is used interchangeably with "reaction chamber," may refer to a special case of a "reaction confinement region" or "reaction area," that is, a physical or chemical attribute of a substrate that permit the localization of a reaction of interest. Reaction confinement regions may be a discrete region of a surface of a substrate that specifically binds an analyte of interest, such as a discrete region with oligonucleotides or antibodies covalently linked to such surface. Reaction confinement regions may be configured or associated with structural attributes such as hollows or wells having defined shapes and volumes which are manufactured into a substrate. These latter types of reaction confinement regions may be microwells or reaction chambers, and may be fabricated using conventional microfabrication techniques, such as those described in the following references: Doering and Nishi (eds.), HANDBOOK OF SEMICONDUCTOR MANUFACTURING TECHNOLOGY, 2nd ed. (CRC Press, 2007); Saliterman, FUNDAMENTALS OF BIOMEMS AND MEDICAL MICRODEVICES (SPIE Publications, 2006); Elwenspoek et al, SILICON MICROMACHINING (Cambridge University Press, 2004); and the like. Various configurations (e.g., spacing, shape and volumes) of microwells or reaction chambers are disclosed in Rothberg et al, U.S. Patent Publication 2009/0127589 and No. 2009/0026082; Rothberg et al, UK. Patent Application GB2461127; and Kim et al., U.S. Pat. No. 7,785,862, which are incorporated by reference. The microwells may have any suitable shape, such as square, rectangular, or octagonal cross sections, and may be arranged as a rectilinear array on a surface. Microwells may also have hexagonal cross sections and be arranged as a hexagonal array, which permit a higher density of microwells per unit area in comparison to rectilinear arrays. In some embodiments, the reaction chamber array comprises $10^2$, $10^3$, $10^4$, $10^5$, $10^6$ or $10^7$ reaction chambers.

An array is a planar arrangement of elements such as sensors or wells. A one dimensional array is an array having one column (or row) of elements in the first dimension and a plurality of columns (or rows) in the second dimension. The number of columns (or rows) in the first and second dimensions may or may not be the same. Preferably, the array used in the present teachings comprises at least 100,000 chambers. Preferably, each reaction chamber has a horizontal width and a vertical depth that has an aspect ratio of about 1:1 or less. Preferably, the pitch between the reaction chambers is no more than about 10 microns. Briefly, in one embodiment microwell arrays may be fabricated as follows. After the semiconductor structures of a sensor array are formed, the microwell structure is applied to such structure on the semiconductor die. That is, the microwell structure can be formed right on the die or it may be formed separately and then mounted onto the die, either approach being acceptable. To form the microwell structure on the die, various processes may be used. For example, the entire die may be spin-coated with a negative photoresist such as Microchem's SU-82015 or a positive resist/polyimide such as HD Microsystems HD8820, to the desired height of the microwells. The desired height of the wells (e.g., about 3-12 µm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. Well height typically may be selected in correspondence with the lateral dimension of the sensor pixel. For example, the wells may have a nominal 1:1 to 1.5:1 aspect ratio, height:width or diameter. Alternatively, multiple layers of different photoresists may be applied or another form of dielectric material may be deposited. Various types of chemical vapor deposition may also be used to build up a layer of materials suitable for microwell formation therein. In one embodiment, microwells are formed in a layer of tetra-methyl-ortho-silicate (TEOS).

The present teachings encompass an apparatus comprising at least one two-dimensional array of reaction chambers, wherein each reaction chamber is coupled to a chemically-sensitive field effect transistor ("chemFET") and each reaction chamber is no greater than 10 µm³ (i.e., 1 pL) in volume. Preferably, each reaction chamber is no greater than 0.34 pL, and more preferably no greater than 0.096 pL or even 0.012 pL in volume. A reaction chamber can optionally be $2^2$, $3^2$, $4^2$, $5^2$, $6^2$, $7^2$, $8^2$, $9^2$, or $10^2$ square microns in cross-sectional area at the top. Preferably, the array has at least $10^2$, $10^3$, $10^4$, $10^5$, $10^6$, $10^7$, $10^8$, $10^9$, or more reaction chambers. The reaction chambers may be capacitively coupled to the chemFETs.

"Polynucleotide" or "oligonucleotide" are used interchangeably and refer to a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions.

Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, HUMAN MOLECULAR GENETICS 2 (Wiley-Liss, New York, 1999).

Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of an appropriate composition for the oligonucleotide or polynucleotide substrates is well within the knowledge of one of ordinary skill, especially with guidance from treatises such as Sambrook et al, MOLECULAR CLONING, 2nd ed. (Cold Spring Harbor Laboratory, New York, 1989), and like references.

"Primer" refers to an oligonucleotide, either natural or synthetic that is capable, upon forming a duplex with a polynucleotide template, of acting as a point of initiation of polynucleic acid synthesis and being extended from its 3' end along the template so that an extended duplex is formed. Extension of a primer may be carried out with a nucleic acid polymerase, such as a DNA or RNA polymerase. The sequence of nucleotides added in the extension process is determined by the sequence of the template polynucleotide. Primers may be extended by a DNA polymerase. Primers may have a length in the range of from 14 to 40 nucleotides, or in the range of from 18 to 36 nucleotides. Primers are employed in a variety of amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach (ed.), PCR PRIMER: A LABORATORY MANUAL, 2nd ed. (Cold Spring Harbor Press, New York, 2003).

While the present teachings has been described with reference to several particular example embodiments, those skilled in the art will recognize that many changes may be made thereto without departing from the spirit and scope of the present teachings. The present teachings are applicable to a variety of sensor implementations and other subject matter, in addition to those discussed above.

wherein the predetermined ordering of dNTP reagent flows comprises an alternate ordering which is not a continuous and ordered repeat of four different dNTP reagent flows, the alternate ordering comprising a same number of flows for each of four different dNTP reagent flows, and at least one flow of each kind of dNTP reagent followed by a flow of the same kind of dNTP reagent after a single intervening flow of a different kind of dNTP reagent, and wherein repetition of the alternate ordering successively occurs at least once to sequence the desired template length.

2. The method of claim 1, wherein repetition of the alternate ordering successively occurs at least twice.

3. The method of claim 1, wherein the predetermined ordering of dNTP reagent flows comprises one of 20, 24, 28 and 32 dNTP reagent flows.

4. A method of sequencing a polynucleotide strand, comprising:
providing the polynucleotide strand with a primer annealed thereto and a polymerase operably bound to the polynucleotide strand;

The invention claimed is:

1. A method for sequencing a template polynucleotide strand comprising:
   (a) disposing a plurality of template polynucleotide strands into a plurality of reaction chambers, such that each reaction chamber has a template polynucleotide strand of the plurality having a sequencing primer hybridized thereto and a polymerase operably bound thereto;
   (b) introducing a known nucleoside triphosphate into each reaction chamber according to a predetermined ordering of dNTP reagent flows;
   (c) detecting sequential incorporation at the 3' end of the sequencing primer of one or more nucleoside triphosphates if the known nucleoside triphosphate is complementary to corresponding nucleotides in the template polynucleotide strands;
   (d) washing away unincorporated nucleoside triphosphates from the reaction chamber; and
   (e) repeating steps (b) through (d) until a desired template length of the plurality of template polynucleotide strands is sequenced;

successively exposing the polynucleotide strand to a first series of flows of four different dNTPs according to a first predetermined ordering; and
successively exposing the polynucleotide strand to a second series of flows of four different dNTPs according to a second predetermined ordering, wherein:
   the second predetermined ordering is different from the first predetermined ordering,
   a same number of flows of each of the four different dNTPs occurs in the first series of flows and the second series of flows, and
   repetition of the first and second predetermined orderings successively occurs at least once to sequence a desired template length,
   wherein one of the first or second predetermined orderings comprises a flow of a nucleotide N, which is followed directly by a flow of a different nucleotide W, which is followed directly by a flow of the same nucleotide N, wherein the N-W-N flow is further followed directly by a flow of a nucleotide Z that is different from N and W.

5. The method of claim 4, wherein the second predetermined ordering comprises an alternate ordering which is not a continuous repeat of the first predetermined ordering of the four different dNTPs.

6. The method of claim 4, further comprising successively exposing the polynucleotide strand to a third series of flows of four different dNTPs according to a third predetermined ordering, wherein the third predetermined ordering comprises an alternate ordering which is not a continuous repeat of the first predetermined ordering of the four different dNTPs or of the second predetermined ordering of the four different dNTPs.

7. The method of claim 4, further comprising successively exposing the polynucleotide strand to a third series of flows of four different dNTPs according to the first predetermined ordering after successively exposing the polynucleotide strand to the second series of flows of four different dNTPs according to the second predetermined ordering.

8. The method of claim 4, wherein repetition of each of the first and second predetermined orderings successively occurs at least twice.

9. The method of claim 4, wherein each of the first and second predetermined orderings of dNTP reagent flows comprises one of 20, 24, 28 and 32 dNTP reagent flows.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Exemplary polynucleotide strand

<400> SEQUENCE: 1
tagcactacg gaacgtgaag gt                                              22

<210> SEQ ID NO 2
<211> LENGTH: 15
<212> TYPE: DNA
<213> ORGANISM: Artificial Sequence
<220> FEATURE:
<223> OTHER INFORMATION: Exemplary polynucleotide strand

<400> SEQUENCE: 2
tagcaacgtg aaggt                                                      15
```